(12) United States Patent
D'Sa

(10) Patent No.: US 7,335,052 B2
(45) Date of Patent: Feb. 26, 2008

(54) METHOD AND SYSTEM FOR DETERMINING AND CONTROLLING A CONTRAST OPACIFICATION IN AN ULTRASONIC EXAMINATION

(75) Inventor: Alwyn P. D'Sa, Cambridge, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/558,731

(22) PCT Filed: May 27, 2004

(86) PCT No.: PCT/IB2004/050796

§ 371 (c)(1),
(2), (4) Date: Nov. 29, 2005

(87) PCT Pub. No.: WO2004/109328

PCT Pub. Date: Dec. 16, 2004

(65) Prior Publication Data

US 2006/0258940 A1 Nov. 16, 2006

Related U.S. Application Data

(60) Provisional application No. 60/476,139, filed on Jun. 5, 2003.

(51) Int. Cl.
*H01R 11/00* (2006.01)

(52) U.S. Cl. ...................................................... 439/502
(58) Field of Classification Search ................ 439/502, 439/59–85, 620–629; 600/459; 361/784; 29/854; 174/250, 255–261
See application file for complete search history.

(56) References Cited

U.S. PATENT DOCUMENTS

| | | | |
|---|---|---|---|
| 5,030,137 A | 7/1991 | Bernhardt | |
| 6,497,667 B1 | 12/2002 | Miller et al. | |
| 6,582,371 B2 * | 6/2003 | Miller | 600/459 |
| 6,952,870 B2 * | 10/2005 | Miller | 29/832 |
| 7,022,080 B2 * | 4/2006 | Marian, Jr. | 600/459 |
| 2003/0028105 A1 | 2/2003 | Miller | |
| 2003/0149364 A1 * | 8/2003 | Kapur et al. | 600/439 |
| 2004/0054289 A1 * | 3/2004 | Eberle et al. | 600/459 |

* cited by examiner

*Primary Examiner*—J. F. Duverne

(57) ABSTRACT

A method and a system for using redundant wire bonds for increasing the reliability of ultrasound transducers are disclosed. An ultrasound transducer assembly having an ultrasound transducer, an integrated circuit, a plurality of wires, and a plurality of bond pads is provided. The integrated circuit includes enlarged lead pads for receiving redundant wire bonds. The ultrasound transducer includes a plurality of bond pads configured to receive the redundant wire bonds. Connecting wires, forming signal paths, connect the enlarged lead pads with the bond pads.

9 Claims, 2 Drawing Sheets

METHOD AND SYSTEM FOR DETERMINING AND CONTROLLING A CONTRAST OPACIFICATION IN AN ULTRASONIC EXAMINATION

CROSS REFERENCE TO RELATED APPLICATION

This application claims the benefit of U.S. provisional application Ser. No. 60/476,139 filed Jun. 5, 2003, which is incorporated herein by reference.

The present invention relates generally to transducers. More specifically, it relates to a method and a system for using redundant wire bonds for increasing the reliability of transducers.

Connections between discrete components generally employ a single connection. Generally, the connection is a single wire formed from copper, gold, or aluminum.

In systems subjected to thermal-cycling conditions, wires are prone to fatigue failure. In many systems, stress resulting from thermal-cycling conditions is directed along the axis of the wire resulting from a mismatch of the coefficients of thermal expansion ("CTE") among system components. A thermal stress to system components commences when the system is powered on. Therefore, it is an object of the present invention to provide a system for increasing the reliability of ultrasound transducers by reducing the average failure rate of the connections between components in an ultrasonic system.

An ultrasound system having increased transducer reliability is hereinafter disclosed. In particular, the system includes an ultrasound probe with at least one ultrasound transducer and at least one integrated circuit assembly. Each integrated circuit assembly includes an integrated circuit, a plurality of connecting wires, and a connecting portion. A plurality of bond pads is disposed along at least one surface of the connecting portion and each bond pad is configured to receive at least two wire ends. The integrated circuit has a plurality of lead pads where each lead pad is configured to receive at least two wire ends. Each wire of the plurality of connecting wires is formed from an electrically conductive material with first and second ends for connecting each lead pad to the corresponding bond pad. The ultrasound probe is configured and adapted to receive at least one ultrasound transducer and at least one integrated circuit assembly.

Additionally, a method of increasing ultrasonic transducer reliability is disclosed herein where an integrated circuit assembly and an ultrasound probe are provided. The integrated circuit assembly includes an integrated circuit, a connecting portion, and a plurality of connecting wires. The integrated circuit has a plurality of lead pads where each lead pad is configured and adapted to receive at least two wire ends. The connecting portion has a plurality of bond pads, where each bond pad is configured and adapted to receive at least two wire ends. The ultrasound probe has at least one ultrasound transducer. The ultrasound probe is configured and adapted to receive the at least one ultrasound transducer and at least one integrated circuit assembly.

The foregoing objects and advantages of the present invention may be more readily understood by one skilled in the art with reference being had to the following detailed description of preferred embodiments thereof, taken in conjunction with the accompanying drawings in which.

Figure 1:
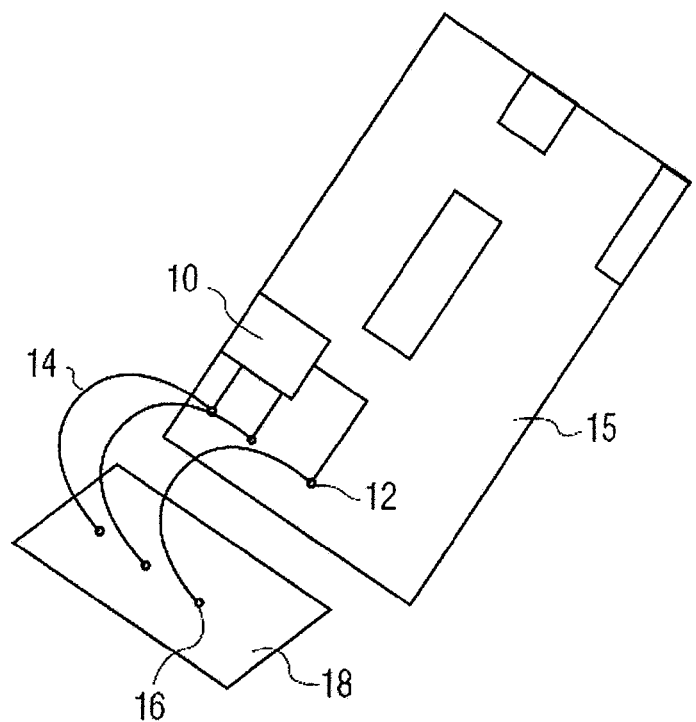
FIG. 1 is a perspective view of a prior art connection between an integrated circuit and a connecting portion.

Several embodiments of the present invention are hereby disclosed in the accompanying description in conjunction with the figures. Preferred embodiments of the present invention will now be described in detail with reference to the figures wherein like reference numerals identify similar or identical elements. As used herein, the term "distal" refers to that portion of the tool, or component thereof which is further from the user while the term "proximal" refers to that portion of the tool or component thereof which is closer to the user.

In a typical prior art system, as shown in FIG. 1, an integrated circuit 10 is disposed on a substrate 15 and includes lead pads 12 that are dimensioned to receive a single wire 14. Each wire 14 has first and second ends where a first end is connected to a lead pad 12 and a second end is connected to a bond pad 16. A printed circuit board 18 includes a plurality of bond pads 16 for connecting components to the printed circuit board 18. These single wire systems generally have a relatively high average system failure rate.

The derivation of this solution requires using the "physics of failure" to understand the causative mechanism, and evoking reliability engineering principles. As discussed hereinabove, in the axis parallel to the wires, the displacement due to a positive temperature coefficient of expansion ("TCE") is generally the greatest. When the probe assembly heats up, i.e. when the system is powered on, the wire-loop from the integrated circuit's lead pad to the bond pad on the printed circuit board is cyclically stretched, thereby applying fatigue-inducing loads that break wires or joints.

The reliability of a one wire system is designated R1. According to reliability engineering, the reliability of a two wire redundant system is determined by the formula $1-(1-R1)^2$ and will typically be much greater than that of a one wire system. By way of example only, if a single wire system has a reliability of R=0.5, then a similarly configured two wire system has a reliability of R=0.75.

Figure 2:
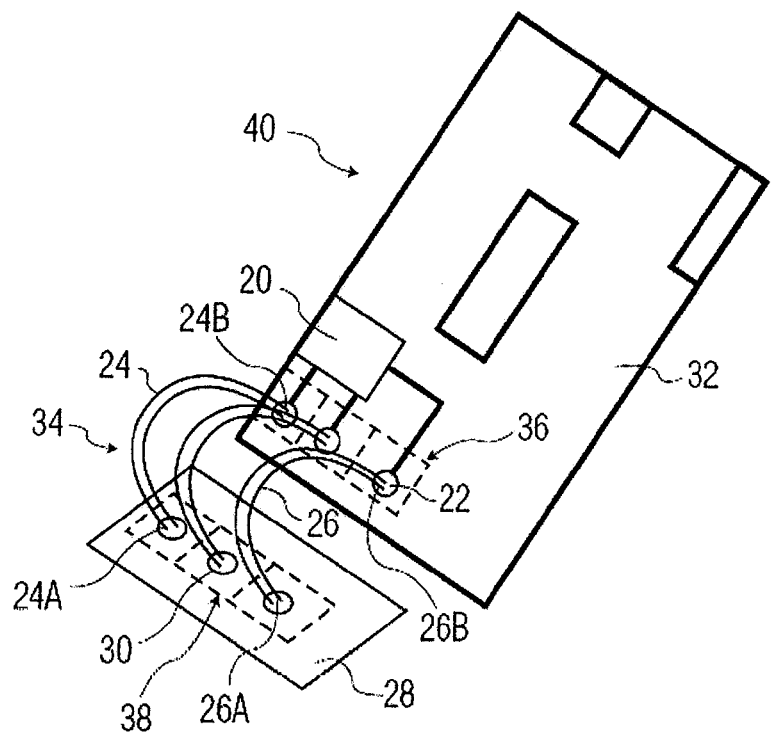
FIG. 2 is a perspective view of an embodiment of an integrated circuit assembly according to the present invention.

According to an embodiment of the present invention, an ultrasound system for increasing ultrasound transducer reliability, and hence, overall system reliability, is hereinafter disclosed. Referring to FIG. 2, a section of an integrated circuit 20 disposed on a corresponding section of a substrate 32 is illustrated. Although only a portion of the integrated circuit is shown in FIG. 2, it is within the scope of the present invention to use the entire "bare" integrated circuit (i.e. the integrated circuit is not disposed within a surrounding package such as a dual-inline package, but is disposed on a substrate material). An integrated circuit assembly 40 according to the present invention includes the substrate 32, the integrated circuit 20, a plurality of connecting wires 24, 26, and the connecting portion 28. The integrated circuit 20 is electrically coupled to a plurality of enlarged lead pads 22 disposed near the outer perimeter of the integrated circuit 20 located on the substrate 32. The plurality of connecting wires 24, 26, form a signal path, for electrically connecting each lead pad 22 with a corresponding bond pad 30 on the connecting portion 28. The number of connecting wires 24, 26 corresponds to the number of lead pads 22 and bond pads 30.

Advantageously, the connecting portion 28 will be a suitably configured printed circuit board having a plurality of bond pads 30 that correspond to the lead pads 22 of the integrated circuit 20. Other configurations of the connecting portion 28 are envisioned including clusters or arrangements of bond pads disposed within the ultrasonic system.

Each wire 24, 26 is formed from a suitable electrically conductive material, such as copper, gold, or aluminum, and includes first ends 24A, 26A and second ends 24B, 26B. By enlarging the lead pads 22, first wire ends 24A, 26A are connected to each lead pad 22. Each bond pad 30 corresponds to a respective lead pad 22 where each bond pad 30 is dimensioned to receive at least two second wire ends 24B, 26B. Second wire ends 24B, 26B are connected to a respective bond pad 30, thereby completing a signal path between the lead pad 22 and the bond pad 30. Signal data is transferred between the integrated circuit 20 and the connecting portion 28 by the connecting wires 24, 26. Wires ends 24A, 26A, 24B, 26B are connected to the lead pads 22 and/or the bond pads 30 by conventional methods, such as wirebonding or soldering.

Figure 3:
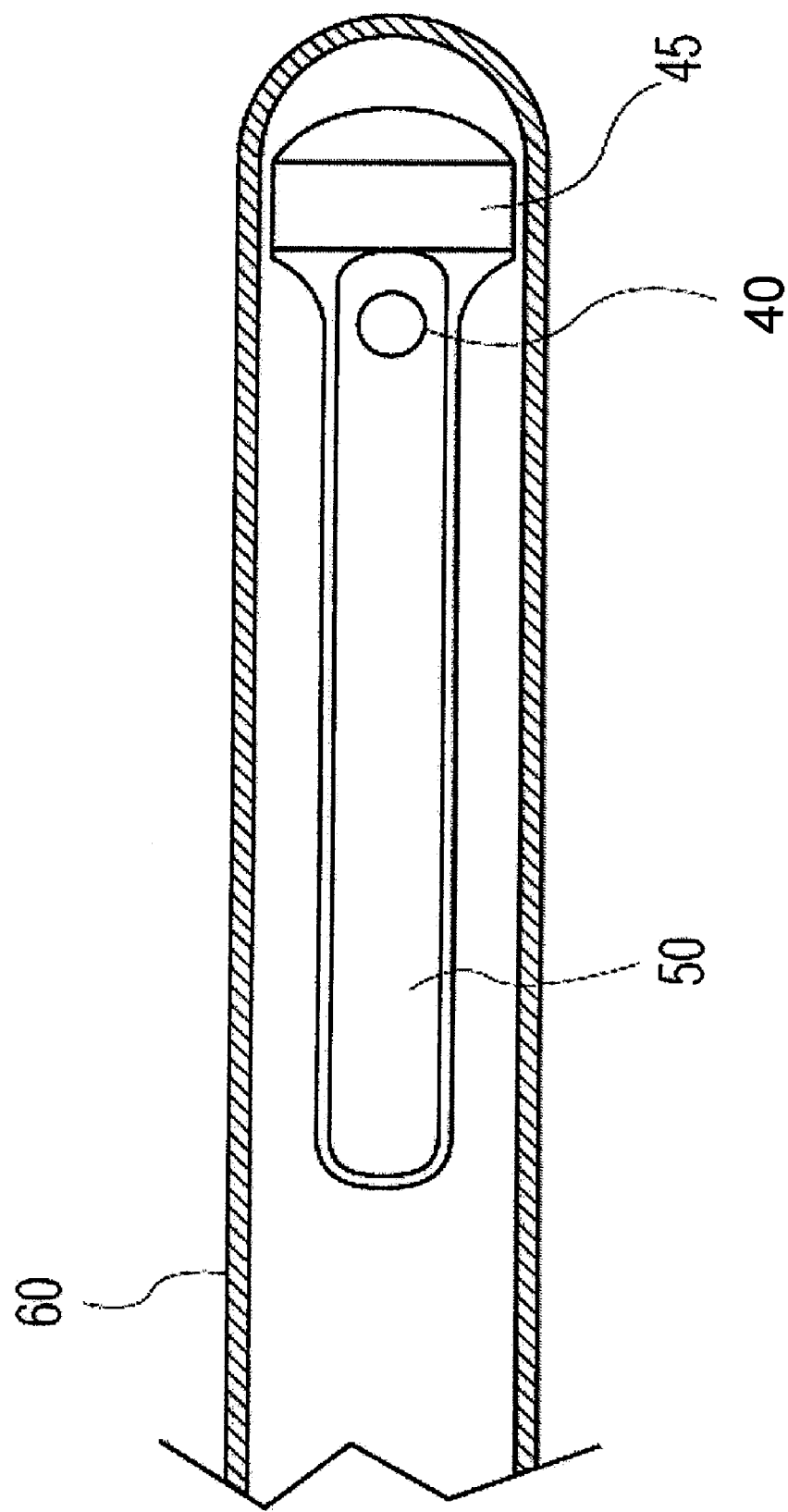
FIG. 3 is a side view of an ultrasound probe showing the location of the integrated circuit assembly of FIG. 2 in the ultrasound probe.

Referring to now to FIG. 3, a preferred embodiment of an ultrasound system is shown. An ultrasound probe housing 60 includes a cavity 50, at least one ultrasound transducer 45, and at least one integrated circuit assembly 40. The at least one ultrasound transducer 45 is disposed in the distal region of the ultrasound probe housing 60. The cavity 50 is disposed along a longitudinal axis of the ultrasound probe housing 60 and is positioned adjacent to and rearward of the at least one ultrasound transducer 45. The at least one integrated circuit assembly 40 is configured and dimensioned to fit within the cavity 50. It is envisioned that the ultrasound probe housing 60 is configured and adapted to include a plurality of ultrasound transducers 45 with a corresponding number of integrated circuit assemblies 40. The plurality of ultrasound transducers 45 may be configured in various array configurations, such as one-dimensional or two-dimensional matrix arrays. Additionally, the ultrasound probe housing 60 includes circuitry for communicating with the integrated circuit assembly 40 and/or the ultrasound transducer 45.

It is preferred that at least the critical signals of an ultrasound transducer include redundant wire bonds in accordance with the present invention. These critical signals include clock signals, data lines, control lines, and power supplies.

In another embodiment, an ultrasound system having increased reliability is disclosed where at least one integrated circuit includes a plurality of enlarged lead pads. Each lead pad is configured and dimensioned to receive the first ends of at least two connecting wires. An ultrasound probe housing includes a corresponding number of bond pads wherein each bond pad is configured and dimensioned to receive the second ends of at least two connecting wires. The bond pads are disposed in the ultrasound probe housing. Connecting wires are disposed in the ultrasound probe housing for transferring signals to and from the integrated circuit. A signal path is formed by the pair of connecting wires between the lead pad and the respective bond pad. Furthermore, the number of connecting wires corresponds to the number of lead pads and bond pads included in the ultrasound system.

A method of increasing reliability of an ultrasound transducer assembly is hereinafter disclosed. According an embodiment of the present invention, an ultrasound probe housing is provided that includes at least one ultrasound transducer. The ultrasound probe housing is configured and dimensioned to receive at least one integrated circuit having enlarged lead pads. A plurality of connecting wires is further included wherein the number of connecting wires corresponds to the number of lead pads of the integrated circuit and the bond pads of the ultrasound assembly. The connecting wires have first and second ends. Each lead pad of the integrated circuit is dimensioned to receive the first ends of at least two connecting wires. Correspondingly, the bond pads of the ultrasound assembly are configured to receive the second ends of at least two connecting wires. A signal path between a lead pad and the corresponding bond pad is formed by at least two wires. The first ends of the signal path are connected to the lead pad. The second ends of the signal path are connected to the bond pad. The ends of the signal path may be joined to the respective lead pad and/or bond pad by conventional methods, such as wirebonding or soldering.

The described embodiments of the present invention are intended to be illustrative rather than restrictive, and are not intended to represent every embodiment of the present invention. Various modifications and variations can be made without departing from the spirit or scope of the invention as set forth in the following claims both literally and in equivalents recognized in law.

The invention claimed is:

1. An ultrasound system having increased transducer reliability, the ultrasound system comprising:
    an ultrasound probe including an ultrasound transducer;
    at least two wires, each wire having a first end and a second end;
    at least one printed circuit board configured and dimensioned to fit within the ultrasound probe, the connecting portion having a plurality of bond pads, each bond pad configured and dimensioned to receive respective first ends of the at least two wires; and
    at least one integrated circuit disposed in the ultrasound system having a plurality of lead pads, each lead pad configured and dimensioned to receive respective second ends of the at least two wires.

2. The ultrasound system of claim 1, wherein the at least one integrated circuit is disposed in the ultrasound probe.

3. An ultrasound system having increased reliability comprising:
    an ultrasound probe including an ultrasound transducer;
    at least one printed circuit board configured and dimensioned to fit within the ultrasound probe and having a plurality of bond pads;
    at least one integrated circuit disposed in the ultrasound probe having a plurality of lead pads; and
    at least one connector for connecting a respective bond pad with a respective lead pad, the connector including at least two wires.

4. The ultrasound system of claim 3, wherein the at least one connecting portion is a printed circuit board.

5. An ultrasound system having increased transducer reliability, the ultrasound system comprising:
    an ultrasound probe including an ultrasound transducer;
    at least two wires, each wire having a first end and a second end; and
    at least one integrated circuit disposed in the ultrasound system having a plurality of lead pads, each lead pad configured and dimensioned to receive respective second ends of the at least two wires; and
    at least one printed circuit board configured and dimensioned to fit within the ultrasound system, the printed circuit board having a plurality of bond pads, each bond pad configured and dimensioned to receive respective first ends of the at least two wires.

6. The ultrasound system of claim 5, wherein the at least one integrated circuit is disposed in the ultrasound probe.

7. The ultrasound system of claim 5, wherein the ultrasound probe further includes a plurality of bond pads, each bond pad configured and dimensioned to receive respective first ends of the at least two wires.

8. The ultrasound system of claim 7, wherein the at least one integrated circuit is disposed in the ultrasound probe.

9. The ultrasound system of claim 6, wherein the at least one connecting portion is a printed circuit board.

* * * * *